//<br>
United States Patent [19]

Armstrong et al.

[11] 4,260,550

[45] Apr. 7, 1981

[54] MODIFIED ROSIN ESTERS

[75] Inventors: David P. Armstrong, Parsippany; Elvin R. Lukenbach, Somerset; Robert J. Verdicchio, Succasunna, all of N.J.

[73] Assignee: Johnson & Johnson Baby Products Company, New Brunswick, N.J.

[21] Appl. No.: 78,634

[22] Filed: Sep. 25, 1979

[51] Int. Cl.$^3$ .................. C09F 5/08; C07C 69/74; C09F 1/00
[52] U.S. Cl. ................... 260/410; 260/101; 260/104; 260/410.6; 260/407; 560/6; 424/70
[58] Field of Search .................. 560/6; 260/101, 104, 260/410.6, 410 R, 407

[56] References Cited

U.S. PATENT DOCUMENTS

| | | | |
|---|---|---|---|
| 2,072,819 | 3/1937 | Humphrey | 260/101 |
| 2,121,294 | 6/1938 | Humphrey | 260/101 |
| 2,251,070 | 7/1941 | Schantz | 260/104 |
| 2,312,732 | 3/1943 | Salathiel | 260/101 |
| 2,359,980 | 10/1944 | Fleck | 260/101 |
| 2,447,750 | 8/1948 | Harris | 560/6 |
| 2,450,079 | 9/1948 | Brown | 260/410.6 |
| 2,508,978 | 5/1950 | Tribble | 260/410.6 |
| 2,950,272 | 8/1960 | Kirkpatrick | 260/104 |
| 3,106,550 | 10/1963 | Bitting | 260/104 |
| 3,541,134 | 11/1970 | Class | 560/6 |

*Primary Examiner*—John F. Niebling
*Attorney, Agent, or Firm*—Steven P. Berman

[57] ABSTRACT

Novel modified rosin esters and a method of preparing these novel compounds are described. The novel compounds are useful in surfactant compositions.

7 Claims, No Drawings

MODIFIED ROSIN ESTERS

BACKGROUND OF THE INVENTION

The present invention relates to modified rosin esters. The modified rosin ester compounds of the present invention can be represented by the following structural formula:

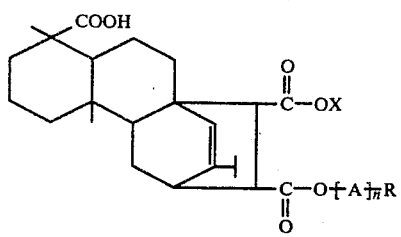

wherein R is hydrogen, alkyl containing from about 8 to 22 carbon atoms, hydroxyalkyl containing from about 8 to 22 carbon atoms, sorbitan monoesters of fatty acids containing from about 8 to 22 carbon atoms or alkyl phenoxy containing from about 8 to 22 carbon atoms; X is hydrogen or an alkali metal salt such as Na, K, Mg or Ca; A is $CH_2-CH_2-O$ or

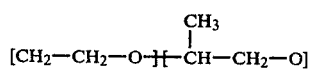

an n is an integer of at least 4 and preferably from about 4 to 5000.

The modified rosin esters of the present invention can be prepared by reacting the levopimaric acid isomer of abietic acid of the formula:

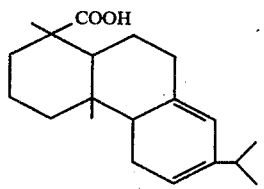

with maleic anhydride of the formula:

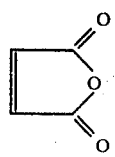

to form a maleated rosin intermediate of the formula:

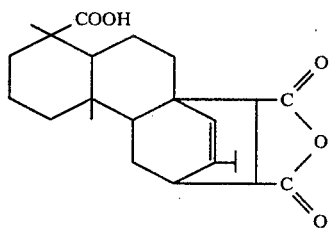

The reaction of the abietic acid with the maleic anhydride is carried out in the presence of a suitable nonprotic solvent such as toluene, xylene, ethyl benzene, and the like and is carried out at a temperature of from about 100° C. to the boiling point of the solvent that is employed.

The maleated rosin intermediate is then reacted with a nonionic surfactant of the formula

wherein R, A and n are as previously defined; to form the desired compounds of the present invention. The reaction of the maleated rosin intermediate with the nonionic surfactant is carried out in the presence of a suitable nonprotic solvent such as toluene, xylene, ethyl benzene and the like and is carried out at a temperature of from about 100° C. to the boiling point of the solvent that is employed.

Specific examples of the novel compounds of the present invention include:

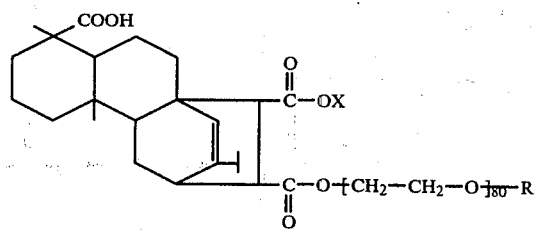

wherein R is sorbitan monopalmitate

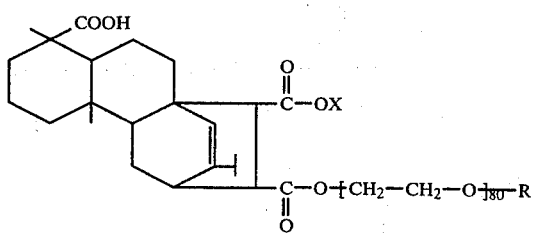

wherein R is sorbitan monolaurate

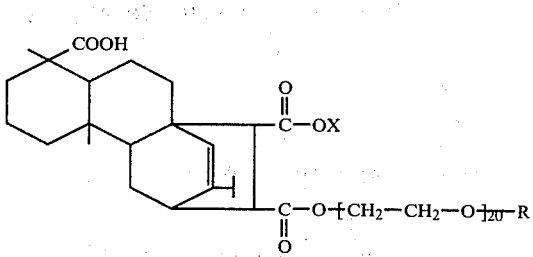

wherein R is sorbitan monococoate

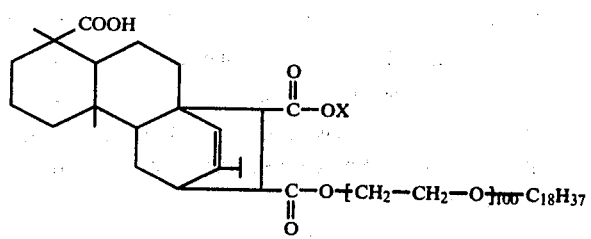
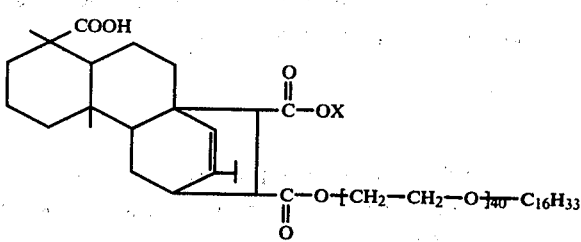
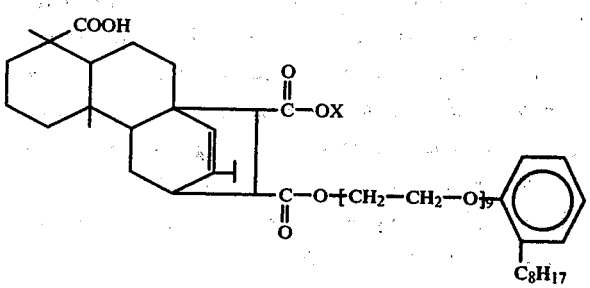
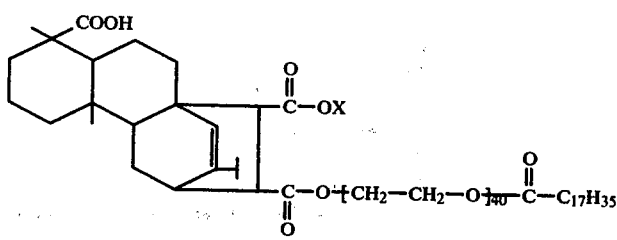
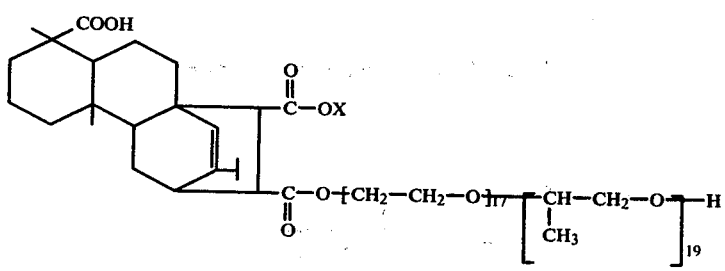
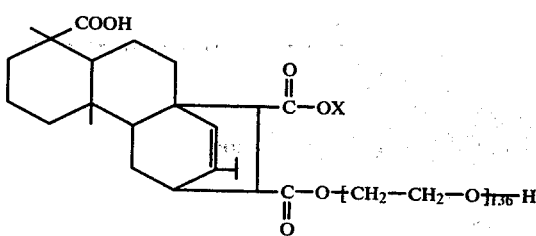
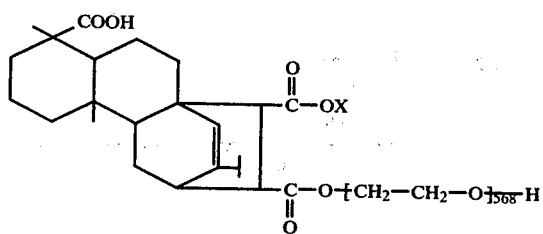

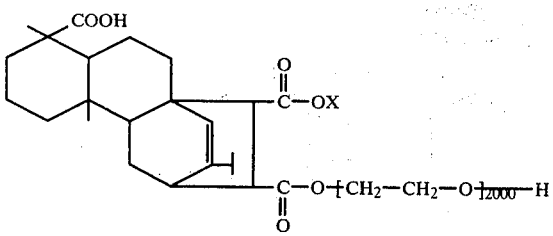

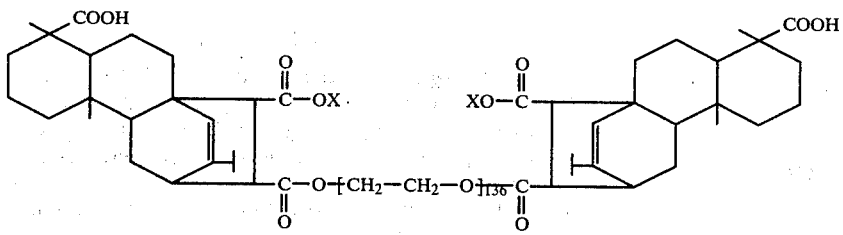

The novel modified rosin ester compounds of the present invention exhibit excellent surfactant properties. These compounds exhibit the desirable cleansing properties and easy "spreadability" and processing characteristics of anionic surfactants while unexpectedly also exhibiting the mildness characteristics of nonionic surfactants. Such is, as stated, unexpected because rosinated materials are normally irritating to the eyes and skin. The excellent "spreadability" characteristics of these modified rosin ester compounds permit them to be extremely useful in gel-type hair care formulations as well as in creme and lotion formulations.

The following examples illustrate the present invention but are not to be construed as imposing any limitations thereon.

EXAMPLE I

Preparation of Maleated Rosin Intermediate 152 grams (0.5 g. moles) of natural wood rosin (Union Camp Corporation, New York), 47 grams (0.5 g. moles) of maleic anhydride and 200 grams of toluene are charged to a flask equipped with a condensor and the mixture is refluxed for four hours. The reaction product is dark amber in color and contains about 44% maleated rosin intermediate in toluene. The structure of this intermediate can be represented as follows:

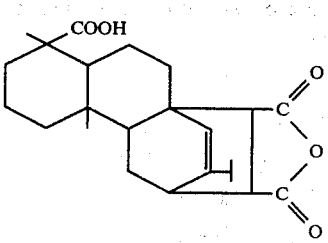

EXAMPLE II

Preparation of Modified Rosin Ester

Into a three-necked flask equipped with a condensor, mechanical stirrer and Dean Stark water receiver are charged 556 grams (0.1 g. moles) of 72% aqueous polyoxyethylene (80) sorbitan monococoate and 400 grams of toluene. The mixture is predried via azeotropic distillation with toluene until all the water is removed. To the anhydrous sorbitan monococoate, 91 grams (0.1 g. moles) of the maleated rosin intermediate of EXAMPLE I are added and the mixture is refluxed for a period of eight hours. After the reaction period, the toluene is removed and a solution of 4 grams (0.1 g. moles) of sodium hydroxide in water (200 ml.) is back-added to yield a final product of about 70% solids which is clear, light yellow in color and water-soluble with a pH of 6.6 at 25° C.

The structure of this product can be represented as follows:

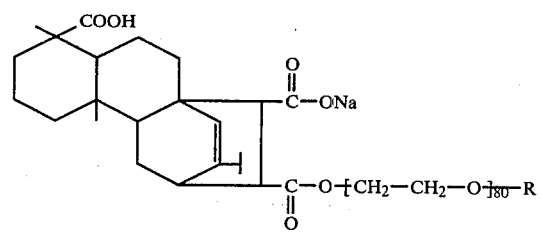

wherein R is sorbitan monococoate.

EXAMPLE III

According to the procedure of EXAMPLE II, 663 grams (0.1 g. moles) of polyoxyethylene (80) sorbitan monopalmitate are reacted with 91 grams (0.1 g. moles) of the maleated rosin intermediate of EXAMPLE I. The resulting product is a visous, light amber to orange color with some turbidity which clears upon heating to 40° C.

The structure of this product can be represented as follows:

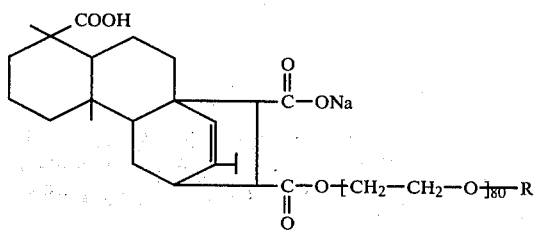

wherein R is sorbitan monopalmitate.

EXAMPLE IV

According to the procedure of EXAMPLE II, 500 grams (0.5 g. moles) of stearyl polyoxyethylene (100) ethanol are reacted with 43 grams (0.5 g. moles) of the maleated rosin intermediate of EXAMPLE I. The resulting product is a white to slightly yellow waxy solid.

The structure of this product can be represented as follows:

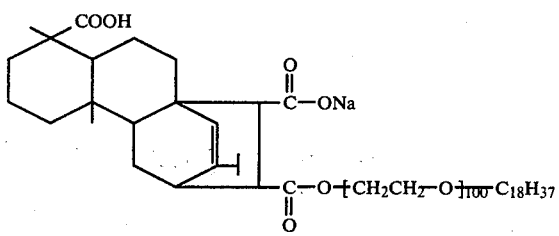

EXAMPLE V

According to the procedure of EXAMPLE II, 0.1 g. moles of cetyl polyoxyethylene (20) ethanol are reacted with 0.1 g. moles of the maleated rosin intermediate of EXAMPLE I.

The structure of the resulting product can be represented as follows:

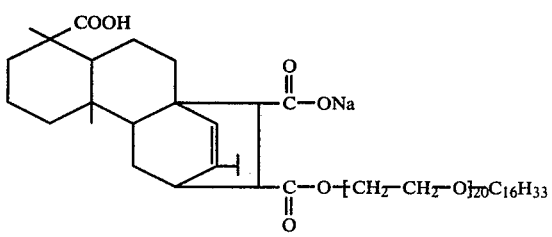

EXAMPLE VI

According to the procedure of EXAMPLE II, 0.1 g. moles of stearoyl polyoxyethylene (40) ethanol are reacted with 0.1 g. moles of the maleated rosin intermediate of EXAMPLE I.

The structure of the resulting product can be represented as follows:

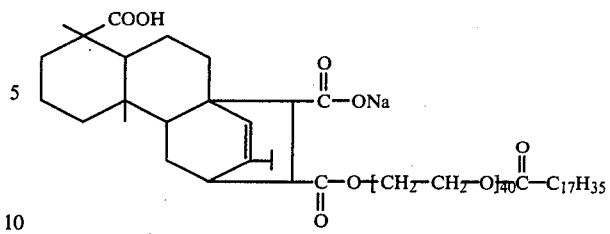

EXAMPLE VII

According to the procedure of EXAMPLE II, 0.2 g. moles of a propylene oxide-ethylene oxide block copolymer of molecular weight of about 1750 are reacted with 0.2 g. moles of the maleated rosin intermediate of EXAMPLE I.

The structure of the resulting product can be represented as follows:

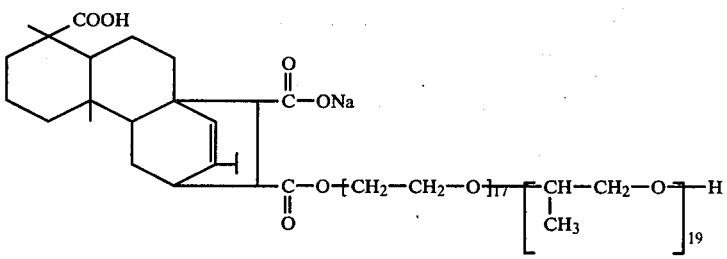

EXAMPLE VIII

According to the procedure of EXAMPLE II, 0.01 g. moles of polyethylene glycol (136) are reacted with 0.01 g. moles of the maleated rosin intermediate of EXAMPLE I.

The structure of the resulting product can be represented as follows:

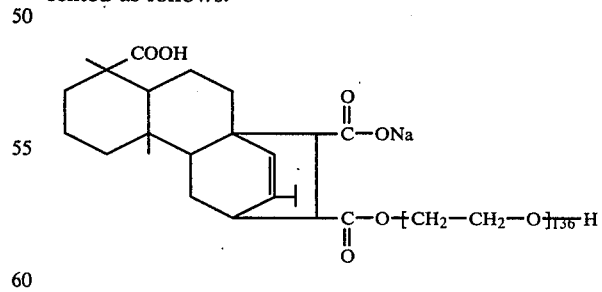

EXAMPLE IX

According to the procedure of EXAMPLE II, 0.02 g. moles of polyethylene glycol (136) are reacted with 0.04 g. moles of the maleated rosin intermediate of EXAMPLE I.

The structure of the resulting product can be represented as follows:

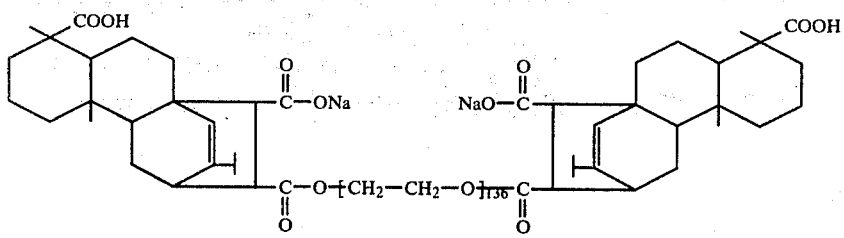

EXAMPLE X

According to the procedure of EXAMPLE V, 0.01 g. moles of polyethylene glycol (2000) are reacted with 0.01 g. moles of the maleated rosin intermediate of EXAMPLE I.

The structure of the resulting product can be represented as follows:

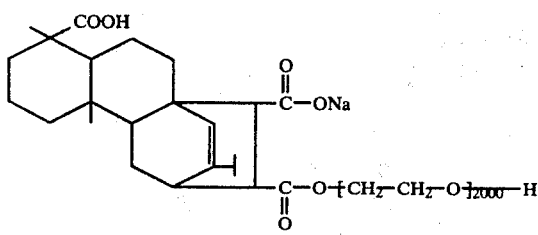

EXAMPLE XI

A hair care product is prepared as follows:

104 grams of a 45% active cocoamidosultaine, 155 grams of a 32% active tridecyl alcohol ether (4.2) sulfate and 182 grams of a 24% active coconut imidazoline are mixed with 207.8 grams of the 72% active rosin modified sorbitan monopalmitate of EXAMPLE II followed by the addition of 0.019 grams of dye and 200 ml. of distilled water. The mixture is heated to 50° C. for twenty minutes and then cooled to 35° C. 1.5 grams of benzyl alcohol/Dowicil 200 preservative mixture and 3 grams of fragrance are added with sufficient deionized water to bring the total mass to 1000 grams.

The finished product is yellow in color with a viscosity of 6150 cps at 25° C. as measured by a Brookfield Viscosimeter. The product exhibits excellent cleansing and foaming properties.

EXAMPLES XII–XVI

The following hair care products are prepared in accordance with the procedure of EXAMPLE XI:

| | % w/w | | | | |
|---|---|---|---|---|---|
| Ingredient | EXAMPLE XII | EXAMPLE XIII | EXAMPLE XIV | EXAMPLE XV | EXAMPLE XVI |
| cocoamidosultaine | 4.5 | 4.5 | 4.5 | 4.5 | 4.5 |
| sodium tridecylether (4.2) sulfate | 4.5 | 4.5 | 4.5 | 4.5 | 4.5 |
| cocoimidazoline 70% active | 5.0 | 5.0 | 5.0 | 5.0 | 5.0 |
| [structure: rosin with C—O—(CH₂—CH₂—O)₈₀—R, R is sorbitan monopalmitate] 70% active | 23.0 | 26.0 | — | — | — |
| [structure: rosin with C—(CH₂CH₂—O)₄₀—C₁₆H₂₃] 70% active | — | — | 20.0 | — | — |

-continued

| Ingredient | % w/w | | | | |
|---|---|---|---|---|---|
| | EXAMPLE XII | EXAMPLE XIII | EXAMPLE XIV | EXAMPLE XV | EXAMPLE XVI |
| [rosin ester structure with COOH and C—(CH₂CH₂—O)₄₀—C—C₁₇H₃₅] | — | — | — | 20.0 | — |
| 70% active polyoxyethylene sorbitan monopalmitate | | | | | 26.0 |
| dye, preservative, fragrance | 0.25 | 0.25 | 0.25 | 0.25 | 0.25 |
| deionized water | q.s. to 100 | q.s. to 100 | q.s. to 100 | q.s. to 100 | q.s. to 100 |
| viscosity cps at 25° C. | 8400 | 6500 | 1300 | 2000 | 6800 |
| yield points dynes/cm² | 14,000 | 18,000 | 13,000 | 17,630 | 26,000 |

The yield points of the above hair care products in dynes/cm² are measured by a Rotoviscometer. The yield point is that point at which a composition becomes liquified or flowable and spreads easily as a result of an applied stress. The higher the yield point of a composition the more difficult it is to spread and therefore the less desirable said composition is as a hair care product.

As can be readily seen from EXAMPLES XII-XVI, the compositions containing the modified rosin ester compounds have significantly lower yield points than the composition containing the similar non-rosinated compound.

EXAMPLE XVII

Hair care products can be tested for ocular irritation by the following modified Draize Test (J. H. Draize et al., Toilet Goods Assn. No. 17, May 1952, No. 1. Proc. Sci. Sect.).

An 0.1 ml. sample of a neutral composition under test is dropped into one eye of an albino rabbit, the other eye serving as a control. Six rabbits are employed for each composition. Observations are made after 1, 24, 48, 72 and 96 hours and 7 days after initial installation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunctiva with a higher number indicating greater ocular irritation and the scores are added to give a total numerical value for each reading for six rabbits and averaged. The averaged score is an indication of the irritation potential of the composition under test. Based on the averaged score, descriptive irritation evaluation may be given, e.g., none, slight, moderate, severe, as the case may be.

When the hair care products of EXAMPLES XI, XII and XIII are treated for ocular irritation in accordance with the above procedure, the following results are obtained:

| Composition | Rating |
|---|---|
| EXAMPLE XI | Slight irritant |
| EXAMPLE XII | slight-moderate irritant |
| EXAMPLE XIII | slight-moderate irritant |

In addition to the preferred embodiments described herein, other embodiments, arrangements and variations within the spirit of the invention and the scope of the appended claims will occur to those skilled in the art.

We claim:

1. A compound of the formula

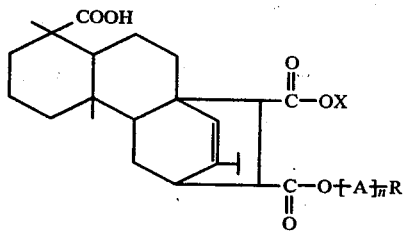

wherein R is alkyl containing from about 8 to 22 carbon atoms, hydroxyalkyl containing from about 8 to 22 carbon atoms, sorbitan monoesters of fatty acids containing from about 8 to 22 carbon atoms or alkyl phenoxy containing from about 8 to 22 carbon atoms; X is hydrogen or an alkali metal salt; A is

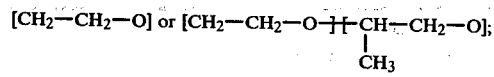

and n is an integer of at least 4.

2. A compound of claim 1 wherein A is [CH₂—CH₂—O].

3. A compound of claim 1 wherein n is an integer of from about 4 to 5000.

4. A compound of claim 1 which compound is of the formula

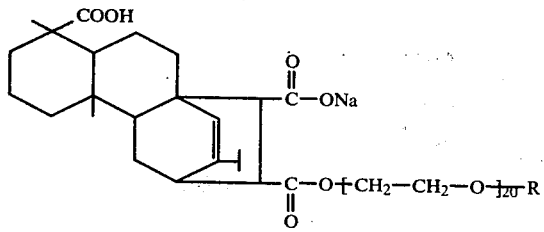

wherein R is sorbitan monococoate.

5. A compound of claim 1 which compound is of the formula

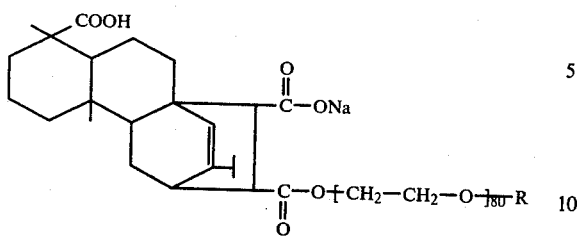

wherein R is sorbitan monopalmitate.

6. A compound of claim 1 which compound is of the formula

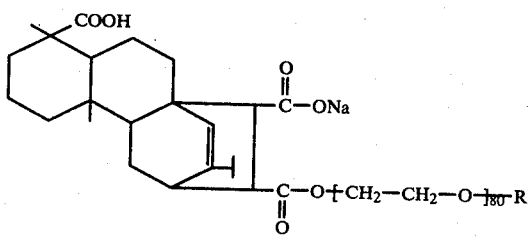

wherein R is sorbitan monolaurate.

7. The process for the preparation of a compound of claim 1 which comprises (a) reacting the levopimaric acid isomer of abietic acid of the formula

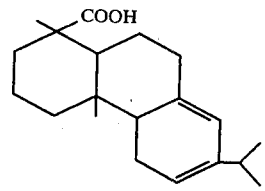

with maleic anhydride of the formula

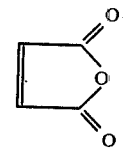

to form a maleated rosin intermediate of the formula

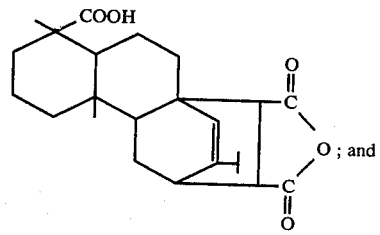

(b) reacting said intermediate with a nonionic surfactant of the formula

HO—[A]$_n$R wherein R, A and n are as defined in claim 1.

* * * * *